United States Patent [19]

Inglis

[11] 4,367,353

[45] Jan. 4, 1983

[54] CATALYTIC HYDROGENATION AND PURIFICATION

[75] Inventor: Hugh S. Inglis, Norton, England

[73] Assignee: Imperial Chemical Industries Limited, London, England

[21] Appl. No.: 968,168

[22] Filed: Dec. 11, 1978

[30] Foreign Application Priority Data

Dec. 21, 1977 [GB] United Kingdom ............... 53187/77

[51] Int. Cl.$^3$ ...................... C07C 7/163; C07C 7/167
[52] U.S. Cl. .................................... 585/258; 585/259; 585/260
[58] Field of Search ........................ 585/259, 260, 258

[56] References Cited

U.S. PATENT DOCUMENTS

| | | | |
|---|---|---|---|
| 1,836,927 | 12/1951 | Linckh et al. | 585/259 |
| 2,671,791 | 3/1954 | Egbert et al. | 585/259 |
| 2,814,653 | 11/1957 | Hogan et al. | 585/259 |
| 2,909,578 | 10/1959 | Andersen et al. | 585/260 |
| 3,098,882 | 7/1963 | Arnold | 585/260 |
| 3,116,342 | 12/1963 | Robinson et al. | 585/259 |
| 3,342,891 | 9/1967 | Poons et al. | 585/259 |
| 3,441,626 | 4/1969 | Kelley | 585/259 |
| 4,126,645 | 11/1978 | Collins | 585/260 |

*Primary Examiner*—Charles F. Warren
*Assistant Examiner*—Raymond Covington
*Attorney, Agent, or Firm*—Cushman, Darby & Cushman

[57] ABSTRACT

In purifying a gaseous unsaturated hydrocarbon stream by selectively hydrogenating more highly unsaturated hydrocarbon impurity contained therein, part of the starting stream is mixed with hydrogen in excess of the stoichiometric requirement to hydrogenate the impurity and passed over a first bed of hydrogenation catalyst, whereafter a second part of the starting stream is mixed with the hydrogen-containing product of the first catalyst and passed over a second bed of hydrogenation catalyst. Using such stepwise feed of hydrocarbon the hydrogen excess can be kept at a high enough level to limit or avoid deactivation of the catalyst, which is preferably supported palladium.

9 Claims, 3 Drawing Figures

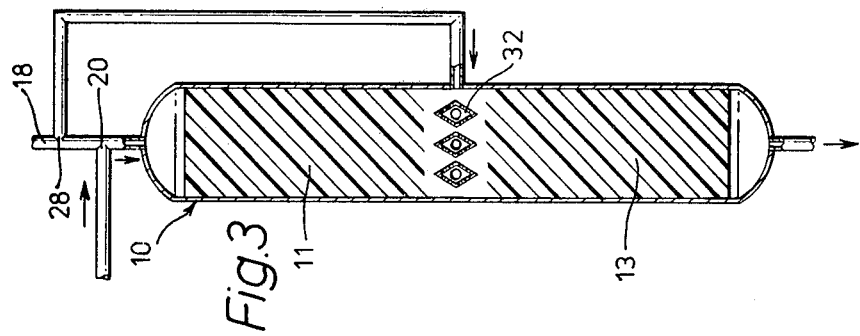
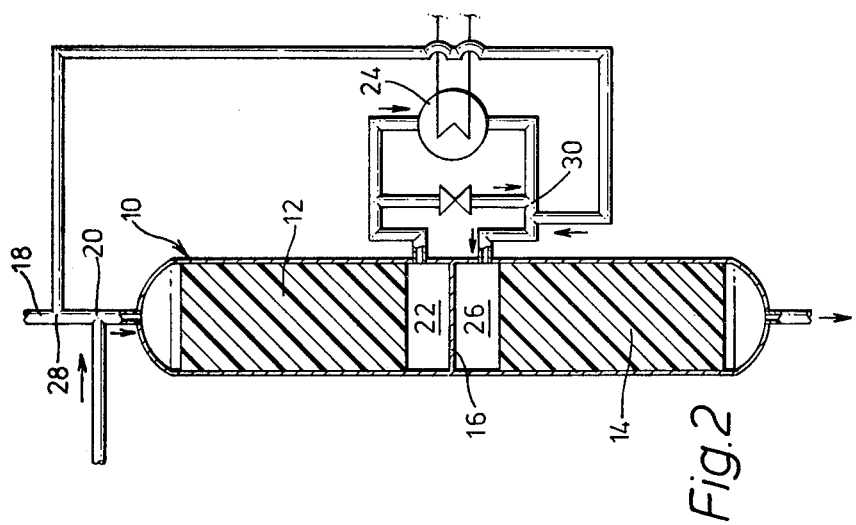
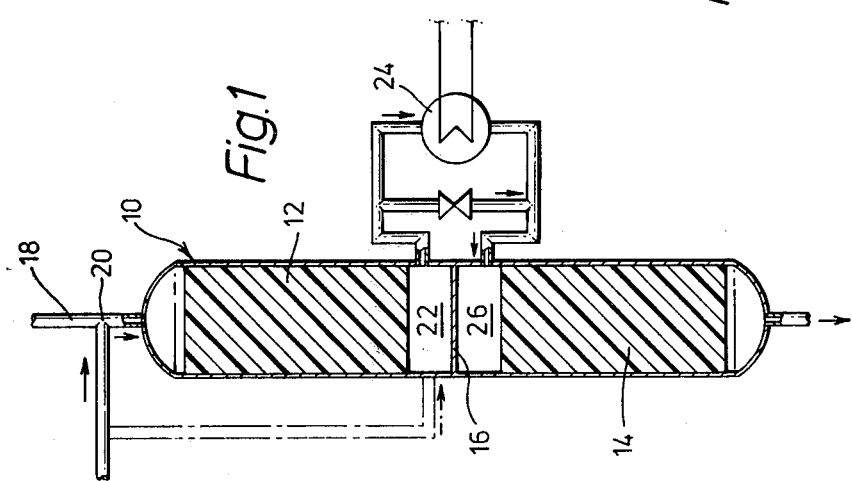

CATALYTIC HYDROGENATION AND PURIFICATION

This invention relates to catalytic hydrogenation and in particular to the purification of unsaturated hydrocarbons by selective hydrogenation of more highly unsaturated hydrocarbons present as impurities.

In such purification processes when applied to streams containing a high proportion of hydrocarbon ("tail-end") it is desirable to use only a small excess of hydrogen, in order to decrease the cost of subsequently removing it. It is found, however, that the process life of catalysts is limited by formation of polymer and/or carbon on the catalyst. The selectivity of the catalyst can also decrease during operation. Typical commercial supported palladium catalysts can be used for as long as 4-6 months before regeneration, but such a period is much less than is obtained in the alternative "front-end" process using a high excess of hydrogen.

We have now devised a way of operating a tail-end hydrogenation so as to lengthen the life of the catalyst between regenerations.

According to the invention a process of purifying a starting gaseous unsaturated hydrocarbon stream by selectively hydrogenating more highly unsaturated hydrocarbon impurities contained therein comprises (a) mixing a first part of the said starting stream with hydrogen in excess of the stoichiometric requirement to hydrogenate the impurities;

(b) reacting the mixture over a first bed of catalyst to give a stream of greater purity and containing unreacted hydrogen;

(c) mixing a second part of the starting stream with the product of step (b), the proportions being such that the hydrogen content is at least sufficient to hydrogenate the impurities; and (d) Reacting the resulting mixture over a second bed of catalyst to give a product stream that is further purified of more highly unsaturated hydrocarbons.

If desired, step (d) could be operated so as to produce a mixture containing a significant excess of hydrogen, whereafter further starting stream could be added and a further reaction step carried out. Indeed, this mixing and reaction step could be repeated yet again. The addition of the second (and, if desired, further) parts of the starting stream could be accompanied by addition of further hydrogen, but this is not preferred since the full bebefit of excess hydrogen in the first reaction step would then not be obtained.

The starting hydrocarbon stream is typically the product of cracking saturated and/or higher hydrocarbons for example ethane, natural gas liquids, LPG or naphtha, followed by fractionation. In this process sequence as used in manufacturing ethylene, the ethylene stream from fractionation contains acetylene as an impurity. When used for manufacturing propylene, the propylene stream from fractionation contains $C_3H_4$ (methyl acetylene and/or allene) as impurity; and similarily butadiene streams contain vinyl acetylene as impurity. The impurity content in the starting hydrocarbon stream is typically up to 6% (for example 0.1 to 3%) and the content of the desired unsaturated hydrocarbon is typically at least 50% especially over 95% all by volume.

The total hydrogen feed to the process should be at least sufficient to hydrogenate to olefin all the acetylenes present and (when the desired product is a mono-olefin) all the diolefins to mono-olefins. Preferably the hydrogen feed is 1.5 to 2.5 times the minimum when the impurity is acetylene and 1.3 to 2.0 times the minimum when the impurity is $C_3H_4$. The hydrogen feed can be at the lower end of these ranges as a result of using the process of the invention.

The temperature is typically in the range 40°-150° C. Since the hydrogenation of the highly unsaturated hydrocarbons is exothermic, the temperature rises as the reaction mixture passes through the catalyst bed if (as is usual) an adiabatic bed is used. The temperature rise is about 60° C. per percent of acetylene and 25° C. per percent of $C_3H_4$ hydrocarbon hydrogenated. Since at too high a temperature there would be significant hydrogenation of the desired product hydrocarbon, the reacting gas is usually withdrawn from contact with catalyst, cooled and then passed through a second bed of catalyst. In the process of the invention the two catalyst beds need not be separated completely, that is, they may be separated only be means for injecting starting hydrocarbon stream; thus the reacting gas is quench-cooled by the injected stream. Such injecion may be at more than one intermediate level. A suitable reactor is that described in our U.K. Pat. No. 1105614, having at one or more positions along the direction of reactant flow a set of perforated hollow bars each having associated with it a sparger for injecting fluid, each hollow bar being large enough in cross section for its interior to constitute a mixing zone, close enough to neighbouring bars or to the reactor walls to cause a substantial part of reaction mixture flowing through the catalyst bed to pass through the interior of the bars and having perforations small enough to ensure that the bar interiors are substantially free of catalyst particles.

The catalyst can be for example one or more of copper and metals from Group VIII of the Periodic Table as set out in "Abridgements of Specifications" published by the UK Patent Office. Palladium is the most widely used catalytic metal for olefin purification by selective hydrogenation and is very suitable for the process of the invention. Other components that may be present with the catalytic metal include copper, silver, gold, zinc, mercury, vanadium, chromium. molybdenum, tungsten, but when palladium is used it is preferably the only catalytic component. Palladium is supported on a refractory oxide, preferably an alumina, possibly with other materials present such as clay or nickel-alumina spinel. The alumina support may have a surface area suitably in the range 1–400 $m^2 g^{-1}$. It appears that known catalyst having support areas in the range 1–100 or 150–400 $m^2 g^{-1}$ are suitable. The palladium content is suitably in the range 0.001 to 3.0% by weight. One very suitable catalyst comprises palladium supported on particulate alumina having a surface area in the range 5 to 200 $m^2 g^{-1}$ (especially 5 to 50 $m^2 g^{-1}$), a helium density of under 5 g $cm^{-3}$, a mercury density of under 1.4 g $cm^{-3}$ and a pore volume of at least 0.4 $cm^3 g^{-1}$, at least 0.1 $cm^3 g^{-1}$ of which is pores of radius over 300 Angstrom units, the palladium being present mainly in region of the catalyst particles not more than 150 microns beneath their geometric surface, as disclosed in our co-pending UK application No. 13965/76 (U.S. Pat. No. 4126645). In this catalyst the palladium-containing part preferably contains 0.01 to 2.0, especially 0.1 to 1.0. w/w of palladium. This catalyst is of the fixed-bed type, in the form of shaped pieces whose largest dimension is in the range 2–12 mm and whose shortest dimension is at least one-third of their largest dimension. Cylindrical compressed pellets or extrusions or approximate spheres are very suitable.

The reaction mixture can contain trace quantities of components effective to increase the selectivity of the palladium catalyst, for example sulphur compounds, hydrogen cyanide or carbon monoxide, as the result of continuous or intermittent injection or of initial treatment of the catalyst. The most useful of these components is carbon monoxide and a suitable content is 4.0 to 500 ppm v/v on the reactant gas mixture.

The pressure at which the process is operated is suitable in the range 1-70 atm. abs., for example 8-40 atm. abs. The total volume/volume space velocity is suitably in the range 500-7000 $h^{-1}$.

The invention is illustrated by the following drawings in which

FIG. 1 represents prior practice, not according to the invention;

FIG. 2 represents one plant for the process of the invention; and

FIG. 3 represents an alternative plant for carrying out the invention.

In FIG. 1, reactor 10 contains two catalyst beds 12 and 14 each in a region of the reactor separated by gas-tight partition from the other region. The hydrocarbon feed 18 receives an injection of hydrogen at 20 and the mixture passes into reactor 10. Hydrogenation takes place to an incomplete extent in bed 12 and the resulting gas at higher temperature is taken from space 22, passed through cooler 24 and returned to the reactor into space 26 above bed 14. If desired, additional hydrogen can be fed to the gas after bed 12, for example by feeding it to space 22, although feeding it to a point in the cooling circuit or to space 26 would be equally practicable. Further hydrogenation then takes place in bed 14 and the reacted gas passes out of reactor 10 at the bottom.

In FIG. 2 the reactor and cooling circuit are similar to those of FIG. 1. The hydrocarbon feed at 18 is, however, divided at 28 into two equal parts. One part receives at 20 an injection of hydrogen at the same flow rate as in FIG. 1, and consequently the mixture entering reactor 10 now has a hydrogen to hydrocarbon ratio twice as great as in FIG. 1. This mixture reacts in bed 12 and is taken out of space 22 and cooled in cooler 24, but before re-entering reactor 10 it receives at 30 an injection of the hydrocarbon feed that was diverted at point 28. There is normally no injection of hydrogen between the catalyst beds. The resulting mixture then undergoes hydrogenation in bed 14.

In FIG. 3 reactor 10 contains catalyst divided into upstream and downstream beds 11 and 13 by gas mixing zones 32. As in FIG. 2, the hydrocarbon feed 18 is divided into two equal parts, one of which receives an injection of hydrogen at the same flow rate as in FIG. 1 and reacts in bed portion 11. Mixing zones 32 have walls perforated with holes small enough to exclude catalyst pellets and are disposed close enough to each other and to the reactor walls to constrain the gas flow into them rather than past them. Inside zones 32 the reacted gas mixes with the other half of the hydrocarbon feed diverted at 28, which is cooler because it has not undergone reaction. The resulting cooled mixture passes out of zones 32 into downstream portion 13 of the catalyst bed, where it reacts further. It then leaves reactor 10 at the bottom.

In an example, a starting gas of volume % composition 90 ethylene, 9 ethane, 1 acetylene is hydrogenated using 2 volumes % of hydrogen at a total space velocity of 2000 volumes of starting gas per volume of catalyst per hour.

In the process of FIG. 1 the hydrogen to acetylene ratio is 2 at the inlet and gradually increases as the acetylene is hydrogenated to thylene. The condition at the inlet end of bed 12 are such that carbon and polymer are laid down on the catalyst and gradually deactivate it. As deactivation proceeds, so further carbon and polymer are laid down on the succeeding undeactivated part of the catalyst.

In the process of FIG. 2 only half the hydrocarbon is fed to bed 12 and accordingly the hydrogen to acetylene ratio is 4 at the inlet and increases more rapidly as acetylene is hydrogenated. A ratio of 4 is sufficient to substantially prevent formation of carbon and polymer. Using a fully selective catalyst there would be 1.5 volumes of hydrogen left at the outlet of bed 12. The second half of the hydrocarbon feed is now added. In the mixture the acetylene content is only 0.5% v/v or slightly over since the fresh gas has been diluted with an equal volume of low-acetylene gas, and the hydrogen to acetylene ratio is 3 or just under 3. These conditions are also such as substantially to prevent carbon and polymer formation.

In the process of FIG. 3 the chemical reactions and mixture proportions are the same as in FIG. 2.

The Table shows typical acetylene and hydrogen relative flow rates in a process according to the invention (FIGS. 2 or 3) in comparison with those in a conventional process (FIG. 1).

TABLE

|  | Invention process | | | Conventional process | | |
|---|---|---|---|---|---|---|
|  | First bed | | Second bed | First bed | | Second bed |
|  | inlet | outlet | inlet | inlet | outlet | inlet |
| total hydrocarbon | 50 | 50 | 100 | 100 | 100 | 100 |
| $C_2H_2$ | 0.5 | 0.05 | 0.55 | 1.0 | 0.3 | 0.3 |
| $H_2$ | 2.0 | 1.55 | 1.55 | 2.0 | 1.3 | 1.3 |

It is assumed that 90% of the acetylene is hydrogenated to ethylene in the first bed of the invention process at a hydrogen to acetylene ratio of 4.0 initially and 70% in the conventional process with that ratio at 2.0 initially, and that no ethylene is hydrogenated. That ratio is thus higher in the initial stages of the invention process at which polymer formation is most serious. The acetylene content of the gas leaving the second bed of each process is a matter of design to suit user's requirements and is therefore not quoted in the Table.

I claim:

1. In a process of purifying a starting gaseous unsaturated hydrocarbon stream substantially devoid of hydrogen by selectively hydrogenating more highly unsaturated hydrocarbon impurity contained therein the improvement resulting in decreased by-product carbon and polymer formation and thereby lengthened catalyst life which comprises (a) dividing the said hydrocarbon stream to provide a first and second stream;

(b) mixing said first hydrocarbon-containing stream with hydrogen in an amount in excess of the stoichiometric requirement to hydrogenate the impurities;

(c) reacting the mixture of step (b) over a first bed of catalyst to give a stream of greater purity and containing unreacted hydrogen;
(d) mixing said second hydrocarbon-containing stream with the product of step (c), the proportions being such that the hydrogen content is at least sufficient to hydrogenate the impurities; and
(e) reacting the resulting mixture of step (d) over a second bed of catalyst to give a product stream that is further purified of more highly unsaturated hydrocarbons.

2. A process according to claim 1 in which the impurity content of the starting stream is in the range 0.1 to 3.0% v/v.

3. A process according to claim 1 in which the content of the desired hydrocarbon in the starting stream is over 95% v/v.

4. A process according to claim 1 in which the starting stream contains ethylene as desired hydrocarbon and acetylene as impurity and the total hydrogen feed is 1.5 to 2.5 times the minimum required to hydrogenate the acetylene to ethylene.

5. A process according to claim 1 in which the starting stream contains propylene as desired hydrocarbon and methylacetylene and/or allene as impurity and the total hydrogen feed is 1.3 to 2.0 times the minimum required to hydrogenate the impurity to propylene.

6. A process according to claim 1 in which the gas from the first bed of catalyst is withdrawn from contact with the catalyst, cooled and then passed through the second bed of catalyst.

7. A process according to claim 1 in which the two catalyst beds are separated by means for injecting starting hydrocarbon stream and the reacting gas is quench-cooled by the injected stream.

8. A process according to claim 1 in which the catalyst contains palladium as the only catalytic component.

9. A process according to claim 8 in which the catalyst comprises palladium supported on particulate alumina having a surface area in the range 5 to 200 $m^2 g^{-1}$, a helium density of under 5 g $cm^{-3}$, a mercury density of under 1.4 g $cm^{-3}$ and a pore volume of at least 0.4 $cm^3 g^{-1}$, at least 0.1 $cm^3 g^{-1}$ of which is pores of radius over 300 Angstrom units, the palladium being present mainly in regions of the catalyst particles not more that 150 microns beneath their geometric surface, and at a content 0.1 to 1.0% w/w in those regions.

* * * * *